US008366646B2

(12) United States Patent
Knyrim

(10) Patent No.: US 8,366,646 B2
(45) Date of Patent: Feb. 5, 2013

(54) MASSAGING DEVICE

(76) Inventor: Jörg Knyrim, Karlsruhe (DE)

( * ) Notice: Subject to any disclaimer, the term of this patent is extended or adjusted under 35 U.S.C. 154(b) by 0 days.

(21) Appl. No.: 13/302,158

(22) Filed: Nov. 22, 2011

(65) Prior Publication Data

US 2012/0071800 A1 Mar. 22, 2012

Related U.S. Application Data

(62) Division of application No. 12/222,130, filed on Aug. 4, 2008.

(30) Foreign Application Priority Data

Sep. 6, 2007 (DE) ..................... 20 2007 012 531 U

(51) Int. Cl.
*A61F 5/00* (2006.01)
*A61H 1/00* (2006.01)
*A61H 19/00* (2006.01)
*A61H 15/00* (2006.01)

(52) U.S. Cl. ............... 601/46; 601/94; 601/112; 600/38

(58) Field of Classification Search .................... 600/38; 601/46, 61, 63, 71, 80, 85, 87, 97, 101–103, 601/112–114, 118–120, 123, 125, 126, 129, 601/130, 137, 94

See application file for complete search history.

(56) References Cited

U.S. PATENT DOCUMENTS

| | | | | |
|---|---|---|---|---|
| 6,632,185 | B2 | 10/2003 | Chen | |
| 7,828,717 | B2 * | 11/2010 | Lee | 600/38 |
| 7,988,605 | B1 | 8/2011 | Wyeroski | |
| 2006/0047181 | A1 | 3/2006 | Hsu | |
| 2007/0142754 | A1 * | 6/2007 | Nan | 601/70 |
| 2007/0179336 | A1 | 8/2007 | Knyrim | |
| 2010/0041944 | A1 * | 2/2010 | Levy | 600/38 |
| 2011/0105837 | A1 * | 5/2011 | Lee | 600/38 |

FOREIGN PATENT DOCUMENTS

| | | |
|---|---|---|
| DE | 200 23 221 | 4/1999 |
| EP | 472965 | 3/1992 |
| NL | 7105209 | 4/1971 |
| WO | WO 2004/036369 | 4/2004 |
| WO | WO 2005/084605 | 9/2005 |

OTHER PUBLICATIONS

EPO Machine Translation of WO2005084605.*

* cited by examiner

*Primary Examiner* — Nicholas Lucchesi
*Assistant Examiner* — Kari Petrik
(74) *Attorney, Agent, or Firm* — Welsh Flaxman & Gitler LLC

(57) ABSTRACT

A massaging device in the shape of a rod with an essentially cylindrical end element with a sleeve. The device has a flexible sleeve and a drive element to produce an oscillating deformation of the sleeve.

2 Claims, 4 Drawing Sheets

(a)
(b)
WL
WL
5
5'
5'

(a)
(b)
WL
WL
5
5'
5'

MASSAGING DEVICE

CROSS REFERENCE TO RELATED APPLICATIONS

The present application is a division of U.S. patent application Ser. No. 12/222,130, filed Aug. 4, 2008, entitled "MASSAGING DEVICE", which is currently pending, which claims the benefit of German Patent Application No. 20 2007 012 531.5, filed Sep. 6, 2007, entitled "MASSAGING DEVICE".

BACKGROUND OF THE INVENTION

The invention relates to a massaging device in the shape of a rod with an essentially cylindrical end element with a sleeve. The sleeve is made of a flexible rubber material and it has a drive element to produce an oscillating deformation of the sleeve.

Such massaging devices for insertion into body cavities, e.g. the vagina, are known in the art (e.g. from EP 0 472 965 A1).

In particular, DE 102004033932 A1 discloses a massaging device in the form of a rod, which comprises an essentially cylindrical end element and a wall or shell made of a flexible rubber material forming the outer surface of the end element. In a first embodiment, the massaging device comprises a drive mechanism consisting of a plurality of jaw-like support elements with bearing and support surfaces, against which the sleeve bears. To create a radial stroke movement of the jaw-like support elements, a shaft is provided that comprises several eccentric sections and engages with the support elements and can be driven by a drive mechanism. Via the radial stroke movement of the jaw-like support elements, three of which are arranged respectively in one plane, an oscillating deformation of the shell relative to a longitudinal axis of the end element is generated radially outward and inward on the end element, so that this deformation takes place along the longitudinal axis of the end element and/or in the peripheral direction of the end element, preferably phase-delayed. In a second embodiment the bearing and support surfaces for the shell are formed by eccentric sections of several shafts, which are oriented with their longitudinal extension in the direction of the longitudinal axis of the end element and can likewise be driven by a drive mechanism.

It is an object of the invention to present a massaging device with a new type of drive mechanism for generating an oscillating deformation of the flexible sleeve of the massaging device.

SUMMARY OF THE INVENTION

An aspect of the massaging device, according to the invention, is that the support elements are formed by several disk-shaped jaw elements adjoining each other along the longitudinal axis or several ball elements arranged along the longitudinal axis, which interact with at least one eccentric section of the at least one shaft to generate a progressive stroke movement of the support elements along the longitudinal axis of the end element.

BRIEF DESCRIPTION OF THE DRAWINGS

The invention is described in more detail below based on exemplary embodiments with reference to the drawings.

DETAILED DESCRIPTION OF THE DRAWINGS

Figure 1:
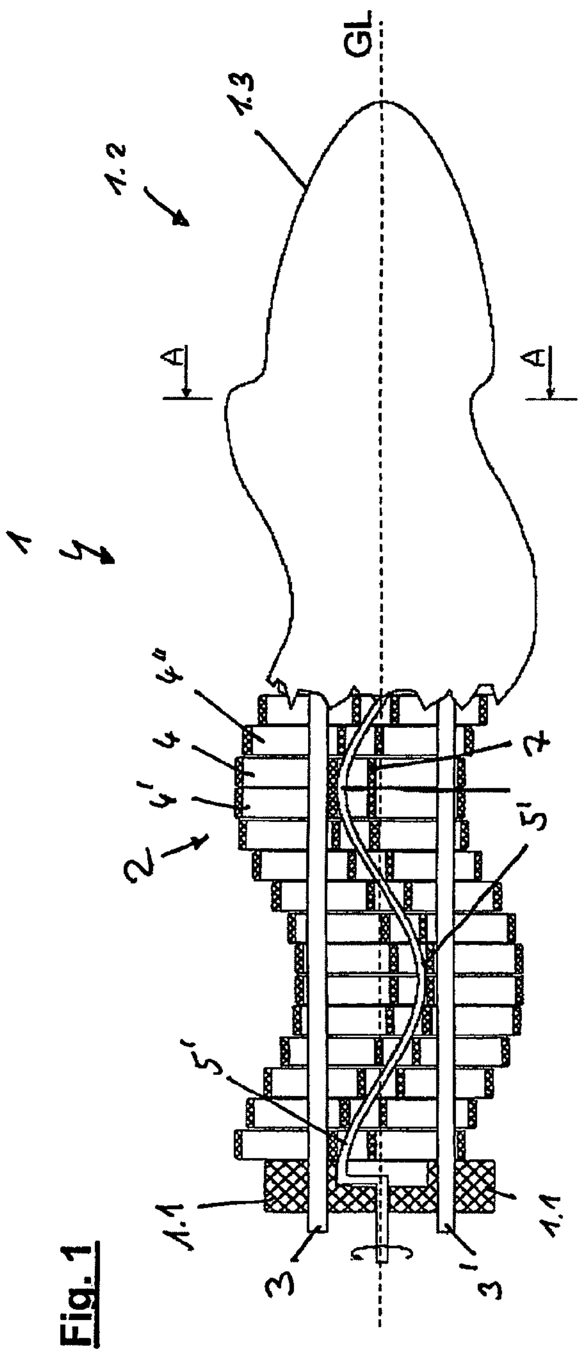
FIG. 1 depicts a massaging device according to the invention in side view, partially in longitudinal section.
Figure 4:
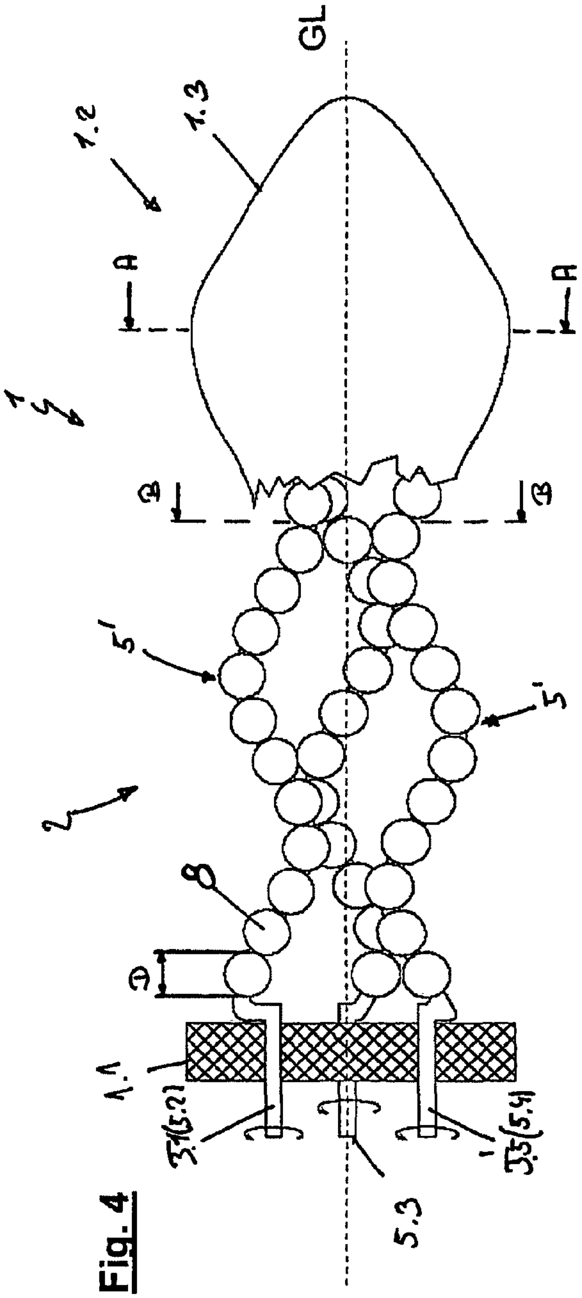
FIG. 4 is a further exemplary embodiment of the invention in a depiction similar to FIG. 1.
Figures 7, 8, 9:
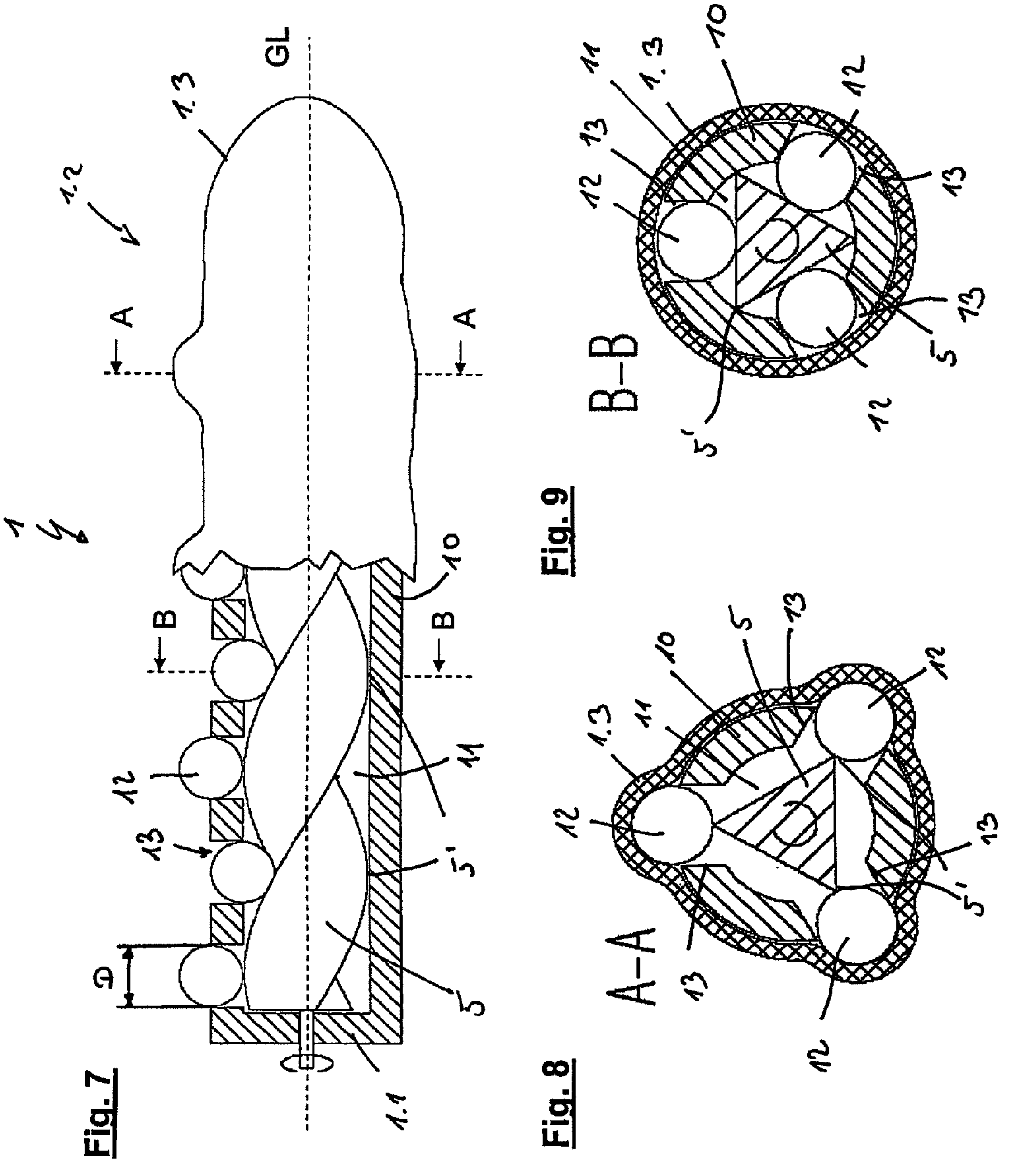
FIG. 7 is a further variation of an exemplary embodiment of a massaging device according to the invention in side view.
FIGS. 8 and 9 are exemplary sections corresponding to the lines A-A and B-B of FIG. 7.

The rod-shaped massaging device generally designated 1 in FIGS. 1, 4 and 7 is made up of a support element 1.1, for example a disk-shaped base element and an adjoining end element 1.2 that is essentially cylindrical. The outer surface of the end element 1.2 is formed by a wall or sleeve 1.3 made of a flexible rubber material. Further, a drive mechanism 2 extending along the longitudinal axis GL of the rod-shaped massaging device 1 is provided for generating an oscillating movement on the end element 1.2.

The drive mechanism 2 comprises in the exemplary embodiment depicted in FIG. 1 several guide and support elements 3, 3', 3'' 3''' protruding over one side of the support element 1.1 in the direction of the longitudinal axis GL, which (support elements) preferably are firmly connected with the support element 1.1. The guide and support elements 3, 3' 3'', 3''' are designed for example in the form of a rod or bar and are oriented along the longitudinal axis GL of the massaging device 1.

Figure 2:
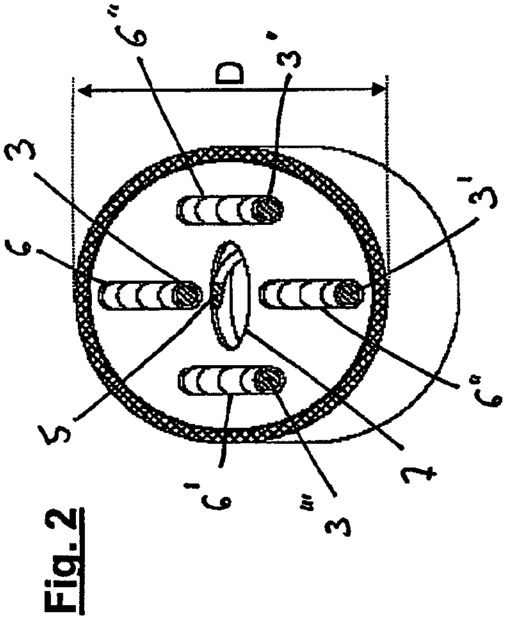
FIGS. 2 and 3 are exemplary sections corresponding to line A-A of FIG. 1.
Figure 3:
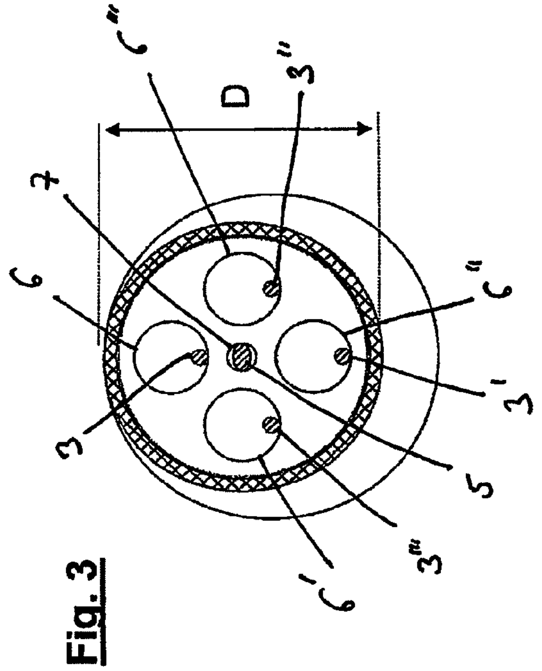

FIGS. 2 and 3 show for example a cross section along the line A-A through the end element 1.2 of the massaging device 1. In the depicted embodiments, preferably first through fourth guide and support elements 3, 3', 3'' 3''' are provided, which are concentrically offset from each other by 90° on the longitudinal axis GL of the massaging device 1, namely so that the respective axis of the first through fourth guide and support element, 3, 3', 3'' 3''' each is at the same distance from the longitudinal axis GL.

In addition to the guide and support elements 3, 3', 3'' 3''' the drive mechanism 2 comprises a plurality of disk-shaped jaw elements 4 arranged consecutively along the longitudinal axis GL of the massaging device 1, which (jaw elements) are placed onto the first through fourth guide and support elements 3, 3', 3'' 3'''. The jaw elements 4 preferably are designed as flat circular disks, each with the same diameter D. The outer or edge surfaces of the jaw elements 4 form support surfaces, which bear against the wall or flexible sleeve 1.3.

To generate the oscillating movement on the end element 1.2, the drive mechanism 2 further comprises a shaft 5, which preferably extends along the longitudinal axis GL of the massaging device 1, the free end facing away from the end element 1.2 being guided through an opening in the support element 1.1 and therefore protruding from the top surface of the support element 1.1 opposite the end element 1.2. The shaft 5 is rotatably mounted in the support element 1.1 and the shaft section protruding from the support element 1.1 in the direction of the end element 1.2 comprises at least one eccentric section 5' for driving the circular disk-shaped jaw elements 4, for which purpose a rotary movement on the longitudinal axis GL or an axis extending parallel to the longitudinal axis GL is generated by a drive unit not depicted in the drawings.

The circular disk-shaped jaw elements 4 each comprise several guide holes 6, 6', 6", 6'" arranged concentrically to their center for holding the guide and support elements 3, 3', 3", 3'", i.e. the guide and support elements 3, 3', 3", 3'", which are stationary in relation to the longitudinal axis GL extend through the guide holes 6, 6', 6", 6'" of the jaw elements 4 and are guided through the inner surfaces of the latter. In addition, a drive hole 7 enclosing the center of each circular disk-shaped jaw elements 4 is provided for holding the shaft 5. Each jaw element 4 can therefore move radially on the longitudinal axis GL nearly independently of the adjacent jaw elements 4', 4", namely in a plane extending perpendicular to the longitudinal axis GL of the massaging device 1. The guide holes 6, 6', 6", 6'" and the drive hole 7 can have different cross sectional shapes depending on the massage motion to be generated. For example, they can be elongated, oval or round.

FIG. 2 shows an exemplary embodiment with a first through fourth elongated guide hole 6, 6', 6", 6'" and an elongated oval drive hole 7 and FIG. 3 shows an exemplary embodiment with a first through fourth round guide hole 6, 6', 6", 6'" and a round drive hole 7. The inner surface of the guide holes 6, 6', 6", 6'" or of the drive hole 7 on the one hand and the diameter and/or the outer form of the guide and support elements, 3, 3', 3", 3'" or of the shaft 5 on the other hand result in a control curve that defines the direction of motion or the radius of motion of the respective jaw element 4 in the plane extending perpendicular to the longitudinal axis GL of the massaging device 1 depending on the angle of rotation of the shaft 5.

Figures 10, 11:
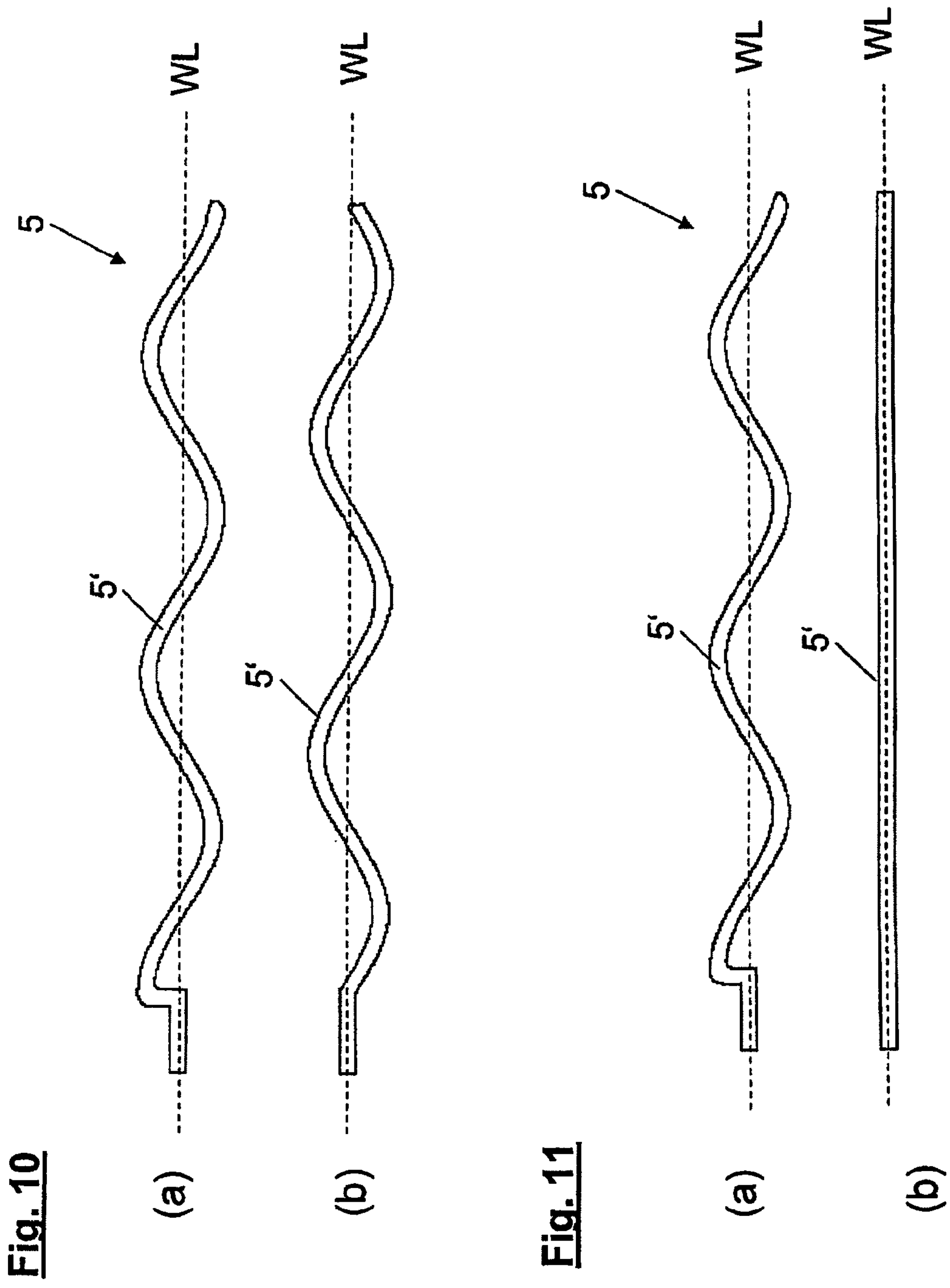
FIGS. 10 *a, b* are two exemplary side views of a first embodiment of a shaft.
FIGS. 11 *a, b* are two exemplary side views of a second embodiment of a shaft.

The shaft 5 can comprise different eccentric sections 5', which are depicted for example in FIGS. 10 (*a*), (*b*) or 11 (*a*), (*b*). In the embodiment according to FIGS. 10 (*a*), (*b*) the shaft 5 follows a spiral-shaped course around the respective longitudinal shaft axis WL. The shaft 5 depicted in FIGS. 11 (*a*), (*b*) has at least one or more eccentric sections 5' lying in the plane E in the form of oscillations around the longitudinal shaft axis WL. By varying the number of the oscillations of the shaft 5 distributed over the total length of the drive mechanism 2 or by varying the gradient of the spirals, the frequency of the oscillating motion of the end element 1.2 can be adjusted at least partially.

The design of the shaft 5 in interaction with the inner surfaces of the guide holes 6, 6', 6", 6'" or of the drive hole 7 results in a displacement of the respective jaw element 4 in the plane extending perpendicular to the longitudinal axis GL of the massaging device 1 and therefore in relation to the end element 1.2 of the massaging device 1, results iii a progressive stroke movement of the jaw elements 4 along the longitudinal axis GL, i.e. the jaw elements 4 follow the respective course of the shaft 5. The stroke movement of the jaw elements 4 produces an oscillating outward and inward deformation of the sleeve 6 in relation to the longitudinal axis GL of the end element 1.2.

Figure 5:
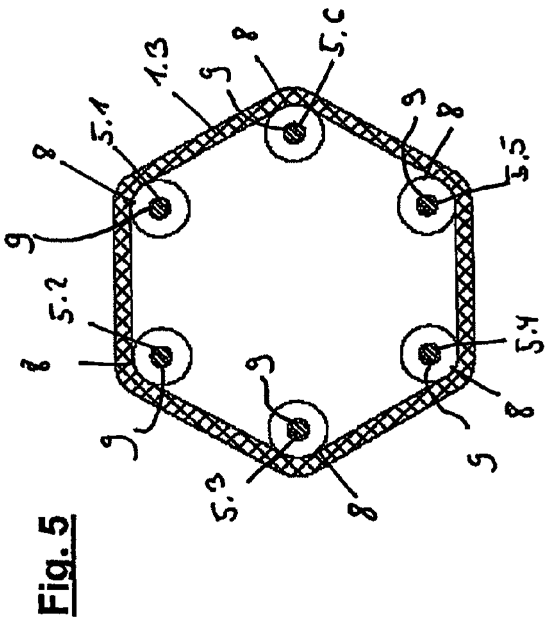
FIGS. 5 and 6 are sections corresponding to the lines A-A and B-B of FIG. 4.
Figure 6:
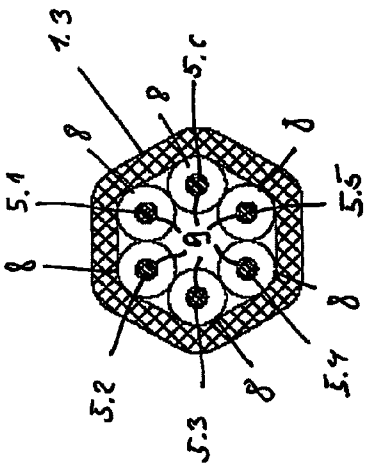

In an alternative embodiment according to FIGS. 4 through 6, instead of the guide and support elements 3, 3', 3", 3'", several shafts 5.1-5.6 are provided, the longitudinal shaft axes WL of which are each arranged parallel to the longitudinal axis GL of the massaging device 1 at the same distance, respectively. The shafts 5.1-5.6 are rotatably mounted in the support element 1.1 and can be driven, preferably synchronously, by means of a drive unit not depicted in FIGS. 4-6. The shafts 5.1-5.6 provided in FIGS. 4-6 each comprise a spiral-shaped eccentric section 5', which extends from the support element 1.1 along the end element 1.2. Such a spiral-shaped shaft type is depicted in FIG. 10, namely in a first side view (a) and in a second side view (b) after rotating 90°.

FIGS. 4, 5 and 6 each show a first through sixth shaft 5.1-5.6 that have a spiral-shaped course and are provided for holding a plurality of ball elements 8. The ball elements 8 each have a guide bore 9, through which the respective shaft 5.1-5.6 passes, i.e. the ball elements 8 are lined up consecutively on the eccentric section 5' of the first through sixth shaft 5.1-5.6 formed by a spiral and therefore form a plurality of support surfaces reproducing the spiral shape of the shaft 5.1-5.6, against which the flexible sleeve 1.3 bears.

The flexible sleeve 1.3 interacting with the outer surface of the ball elements 8 therefore forms for example a polygon with a hexagonal cross section (FIGS. 5 and 6), the circumference of which is dependent on the distance from the respective ball element 8 to the longitudinal axis L of the massaging device 1. Depending on the angle of rotation of the first through sixth shaft 5.1-5.6, the flexible sleeve 1.3 expands or contracts by means of the ball elements 8 bearing against it, causing the diameter of the rod-shaped massaging device 1 to periodically expand or contract, resulting in a progressive oscillating stroke movement along the longitudinal axis GL.

FIGS. 5 and 6 illustrate a cross section through the end element 1.2 of the massaging unit 1 depicted in FIG. 4 along the line A-A and B-B, FIG. 5 showing the maximum achievable expansion of the flexible sleeve 1.3 by means of the first through sixth shaft 5.1-5.6 or the ball elements 8 and FIG. 6 showing the fully contracted flexible sleeve 1.3. By turning the shafts 5.1-5.6 preferably synchronously, the ball elements 8 located on the shafts 5.1-5.6 move in a plane extending perpendicular to the longitudinal axis GL, namely alternately from the outside toward the inside and vice versa.

In a preferred embodiment the eccentric sections 5' of the shafts 5.1-5.6 are arranged so that during operation of the massaging device 1 both a maximum and a minimum expansion of the flexible sleeve 1.3 at different locations on the end element 1.2 are possible nearly at the same time.

Alternatively, however, the eccentric sections 5' of the shafts 5.1-5.6 can also be oriented in the same direction, i.e. the spiral-shaped eccentric sections 5' of the shafts 5.1-5.6 extend parallel to each other. This results in an overall spiral-shaped movement of the flexible sleeve 1.3 with a constant diameter D.

In a further alternative embodiment of the massaging device 1 according to FIG. 7 the drive mechanism 2 consists of a thick-walled tube element 10 extending along the longitudinal axis GL, which preferably has a round cross section. The rod-shaped tube element 10 forms a preferably cylindrical hollow space 11 for holding a shaft 5, which (hollow space) is closed by the support element 1.1. The free end of the rod-shaped tube element 10 opposite the support element 11 can be either open or likewise closed.

The shaft 5 has a drill-like form and is likewise mounted rotatably in the support element 1.1. The eccentric section 5' is formed by an edge of the shaft 5 forming a helical line extending around the longitudinal axis GL of the massaging device 1, namely within the cylindrical hollow space 11. The shaft 5 has a non-circular cross section, for example a triangular cross-section, which is twisted along the shaft axis WL or longitudinal axis GL of the massaging device 1 so that the extremities or corner points of said cross section lie on a helical line around the shaft axis WL.

Further, the outer wall of the tube element 10 comprises several guide bores 13, which are distributed along the longitudinal axis GL of the massaging device 1, and for example several guide bores 13 are provided in one plane extending perpendicular to the longitudinal axis GL, respectively. The guide bores 13 are provided for holding and guiding preferably solid ball elements 12, which bear against at least one of the eccentric sections 5'. The ball elements 12 therefore interact with the flexible sleeve 1.3 surrounding the thick-walled tube element 10 and with the drill-like shaft section 5'. The ball elements 12 bear against the outer surface of the eccentric section 5' and are pressed by the flexible sleeve 1.3 through the respective guide holes 13 of the tube element 10 onto the outer surface of the eccentric section 5'.

FIGS. 8 and 9 show the two reversal points of the stroke movements of the flexible sleeve 1.3 that can be produced by the shaft section 5'. In the present embodiment, three ball elements 12, offset from each other by 120°, are arranged respectively in a plane extending perpendicular to the longitudinal axis GL of the massaging device 1. Several such ball arrays adjoin along the longitudinal axis GL.

In FIG. 8 the ball elements 12 have reached the greatest distance from the longitudinal axis GL, in that they protrude beyond the outer surface of the tube element 10 and are still partially pressed by the flexible sleeve 1.3 into the guide bores 13. FIG. 9 shows the state in which the ball elements 12 are completely held within the tube element 10 or its hollow space 11, so that the flexible sleeve 1.3 bears directly on the outer surface of the tube element 10.

Changing from the outward position depicted in FIG. 8 to the inward position depicted in FIG. 9 and vice versa results in an oscillating motion of the flexible sleeve 1.3 on the end element 1.2, which progresses along the longitudinal axis GL of the massaging device 1 due to the drill-like form of the shaft 5. The phase of the stroke movement of the ball elements 12 therefore changes in longitudinal direction GL depending on the current rotary position of the shaft 5, namely from the inward position to the outward position and intermediate positions.

The diameter of the guide bores 13 is adapted to the diameter of the ball elements 12. In a preferred embodiment the guide bores 13 extend slightly conically from the hollow space 10 outward, so that the outer radius of the guide bores 13 is smaller than the inner radius of the respective guide bore 13. This prevents the ball elements 12 from coming out of the guide bores 13.

Instead of one shaft 5 with a drill-like form, several spiral-shaped shafts 5.1-5.3 can be provided in a massaging device according to FIGS. 7, 8 and 9 concentrically to the longitudinal axis GL of the massaging device 1, as for example in the manner depicted in FIGS. 10 (*a*) and (*b*), where three such spiral-shaped shafts 5.1-5.3 are arranged and synchronously driven to achieve a stroke movement that is comparable to the use of a drill-like shaft 5.

The invention was described above based on exemplary embodiments. It goes without saying that numerous modifications and variations are possible without abandoning the underlying inventive idea upon which the invention is based.

REFERENCE LIST

1 massaging device
1.1 support element
1.2 end element
1.3 sleeve or wall
2 drive mechanism
3, 3', 3'', 3''' guide and support element
4 disk-shaped jaw elements
5 shaft
5' eccentric section
5.1-5.6 first through sixth shaft
6, 6', 6'', 6''' guide hole
7 drive hole
8 ball element
9 guide bore
10 tube element
11 cylindrical hollow space
12 ball elements
13 guide bores
WL shaft axis
D diameter
GL longitudinal axis

What is claimed is:

1. A massaging device in the shape of a rod with an essentially cylindrical end element, with a sleeve forming an outer surface of the end element and made of a flexible rubber material and with a drive mechanism for generating a movement on the end element for an oscillating deformation of the sleeve in relation to a longitudinal axis (GL) of the end element radially outward and inward, so that the oscillating deformation takes place along the longitudinal axis (GL) of the end element or in a circumferential direction of the end element, the drive mechanism having a plurality of bearing and support surfaces bearing against the sleeve, which are formed by a plurality of support elements and which are driven by at least one shaft, wherein the support elements are formed by several ball elements arranged along the longitudinal axis (GL), which interact with at least one eccentric section of the at least one shaft generate a progressive stroke movement of the support elements along the longitudinal axis (GL) of the end element, wherein the several ball elements are arranged respectively in one common plane perpendicular to the longitudinal axis (GL) of the end element and form a group of ball elements, which interact with the at least one eccentric section to generate a progressive radial stroke movement of the group of ball elements along the longitudinal axis (GL) of the end element, wherein several spiral shafts are provided for holding a plurality of the ball elements, longitudinal shaft axes (WL) of which, are arranged parallel to the longitudinal axis (GL) of the massaging device and which can be driven synchronously to each other.

2. The massaging device according to claim 1, wherein a plurality of such groups is provided consecutively along the longitudinal axis (GL) of the end element.

* * * * *